(12) United States Patent
Howard et al.

(10) Patent No.: US 8,414,691 B2
(45) Date of Patent: *Apr. 9, 2013

(54) SYSTEM AND METHOD EXTRACTING AND EMPLOYING COMPRESSION HEAT IN BIOGAS TREATMENT PLANT EQUIPMENT

(75) Inventors: Lowell Howard, Redmond, WA (US); Jeffrey Wetzel, Lake Stevens, WA (US); Ronald Drake, Helena, MT (US)

(73) Assignee: ESC Enviroenergy, LLC, Redmond, WA (US)

( * ) Notice: Subject to any disclaimer, the term of this patent is extended or adjusted under 35 U.S.C. 154(b) by 292 days.

This patent is subject to a terminal disclaimer.

(21) Appl. No.: 12/879,393

(22) Filed: Sep. 10, 2010

(65) Prior Publication Data

US 2011/0005393 A1 Jan. 13, 2011

Related U.S. Application Data

(63) Continuation-in-part of application No. 12/215,633, filed on Jun. 27, 2008, now Pat. No. 7,806,964.

(60) Provisional application No. 60/937,587, filed on Jun. 27, 2007.

(51) Int. Cl.
*B01D 53/04* (2006.01)

(52) U.S. Cl.
USPC .................. 95/115; 95/141; 95/148; 96/146

(58) Field of Classification Search .................... 95/114, 95/115, 141, 148; 96/143, 144, 146
See application file for complete search history.

(56) References Cited

U.S. PATENT DOCUMENTS

| | | | | |
|---|---|---|---|---|
| 4,000,990 A * | 1/1977 | Bingham | ......................... | 95/103 |
| 4,770,676 A * | 9/1988 | Sircar et al. | ....................... | 95/99 |
| 4,784,672 A * | 11/1988 | Sircar | ............................... | 95/97 |
| 5,059,405 A * | 10/1991 | Watson et al. | ................ | 423/210 |
| 5,451,249 A * | 9/1995 | Spiegel et al. | .................. | 95/117 |
| 5,846,295 A * | 12/1998 | Kalbassi et al. | ................ | 95/105 |
| 5,938,819 A * | 8/1999 | Seery | .............................. | 95/104 |
| 6,221,130 B1 * | 4/2001 | Kolodziej et al. | ................ | 95/41 |
| 6,984,258 B2 * | 1/2006 | Niclout et al. | ................... | 95/115 |
| 7,806,964 B2 * | 10/2010 | Howard et al. | ................. | 95/115 |
| 2008/0257158 A1 * | 10/2008 | Howard | .......................... | 96/127 |

* cited by examiner

*Primary Examiner* — Frank Lawrence, Jr.
(74) *Attorney, Agent, or Firm* — Dean A. Craine

(57) ABSTRACT

The system and method for recycling and using the heat from compressed gas produced by a biogas treatment plant. The system includes a biogas cleaning stage and a plurality of compression and heat exchanger stages that allows the heat generated by compressed gases to be harvested. After the heat is harvested, it is delivered to a jacketed vessel containing media used to remove contaminants from the biogas. The media inside the jacketed vessel requires regeneration or stripping of harmful VOCs and other contaminants picked up from the biogas. The system also includes an inert gas generator that creates hot inert gas that is delivered to the jacketed vessel that heats the media located therein to remove contaminants. Because the jacket vessel and the media are simultaneously heated, the system's heat-up time is reduced The system also includes a heat exchanger that partially recovers the heat from the inert gas.

18 Claims, 4 Drawing Sheets

SYSTEM AND METHOD EXTRACTING AND EMPLOYING COMPRESSION HEAT IN BIOGAS TREATMENT PLANT EQUIPMENT

This is a continuation-in-part application based on the utility patent application filed on Jun. 27, 2008 (Ser. No. 12/215,633) which claimed the benefit of U.S. Provisional Application No. 60/937,587 filed on Jun. 27, 2007 and now U.S. Pat. No. 7,806,964.

BACKGROUND OF THE INVENTION

1. Field of the Invention

This invention pertains to heat recycling systems, and more particularly to heat recycling systems used in biogas treatment systems.

2. Description of the Related Art

It is well known that compression of gases produce heat. In systems that generate a large amount of compressed gas, the amount of heat produced can be substantial.

In a landfill or sewage treatment plant, low pressure fuel gases are produced that must be compressed for use with power generation systems, such as reciprocating engine generators, microturbines, and large gas fired turbine generators. Gas compression can encompass 1, 2, or 3 separate stages, depending on the ultimate required pressure of the gas. Typically, the heat produced by compressing the gas is either not recovered, or is only partially collected and used by heat exchangers. Unfortunately, a large portion of the heat is wasted and released into the atmosphere.

The invention disclosed herein pertains to systems used to more efficiently capture the wasted heat and utilize it in a biogas treatment system for increased economy.

SUMMARY OF THE INVENTION

It is an object of the present invention to provide a system for harvesting and cleaning contaminated biogas.

It is another object of the present invention to provide such a system where the heat of compression of the biogas is harvested and used to remove contaminants from the biogas.

It is another object of the present invention to provide such a system that enables the operator to easily switch between decontamination (media regeneration) and gas purification (scrubbing) modes.

These and other objects are met by the method and system for use of compression heat generated in a biogas treatment plant disclosed herein that includes a heat exchanger located at each stage of compression designed to utilize all of the gas flow and to harvest the heat produced when compressing the cleaned biogas and then used to harvest the heat in gases delivered to the heat exchangers.

After the heat is harvested after each compression stage, it can be conveyed as a hot fluid to a jacket surrounding a vessel containing media that requires thermal regeneration or stripping of harmful volatile organic components (VOCs) picked-up during the purification (scrubbing) mode of contaminated landfill or municipal digester gas. The media inside the vessel is cleaned or recycled by a hot inert gas produced by a combination inert gas generator and VOC destruction unit.

The harvesting and conveyance of the heat of compression of the gases to the jacket surrounding the vessel (indirect contact) and simultaneously heating the vessel's interior containing the spent media through the hot gas from another source (direct contact), reduces the heat-up time for the thermal regeneration cycle. This, in turn, reduces the overall cycle time to regenerate the spent media and return the vessel to service in the gas purification mode.

DESCRIPTION OF THE PREFERRED EMBODIMENT(S)

A biogas system 10 for capturing and conveying the heat from gas compressors to aid or drive the removal of moisture and VOC/organosilicon compounds from biogas 12. The system 10 transmits the heated gases from a plurality of compressors 15, 50, 60 used at different stages of the system 10. Heat from the compressors 15, 50, and 60 is then used to provide uniform and constant temperature control.

Figure 1:
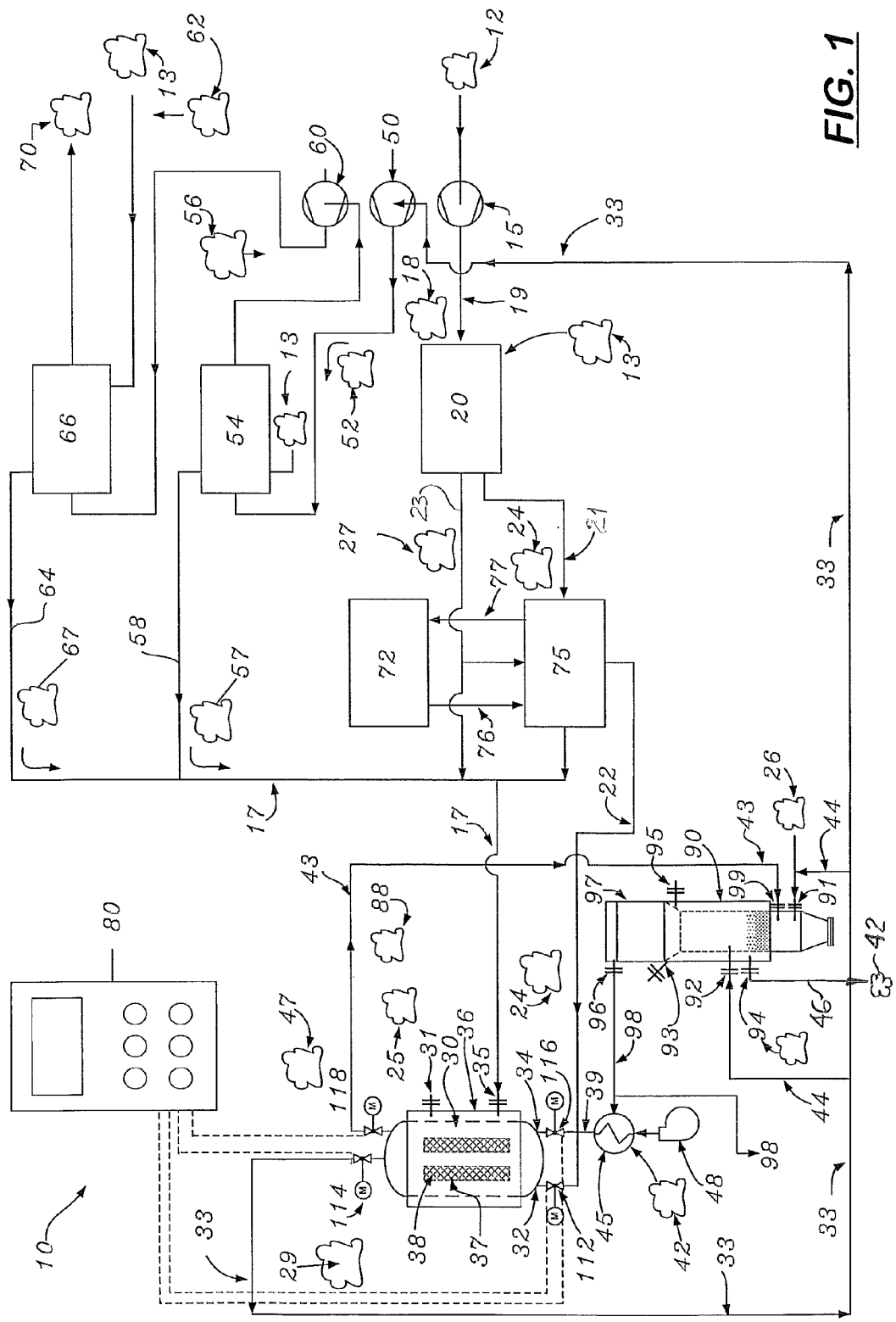
FIG. 1 is a diagram of the entire system for capturing and conveying the heat from gas compressors to aid or drive moisture and VOC/organosilicon compound removal from biogas.
Figure 2:
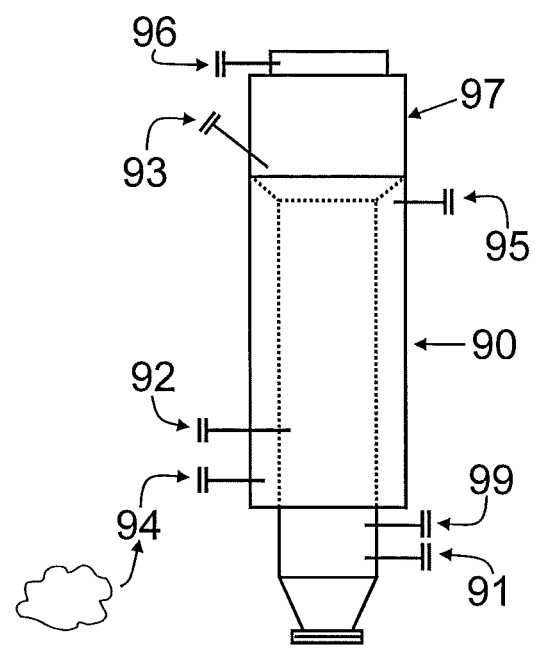
FIG. 2 is an illustration showing the inert gas generator/VOC destruction unit.
Figure 3:
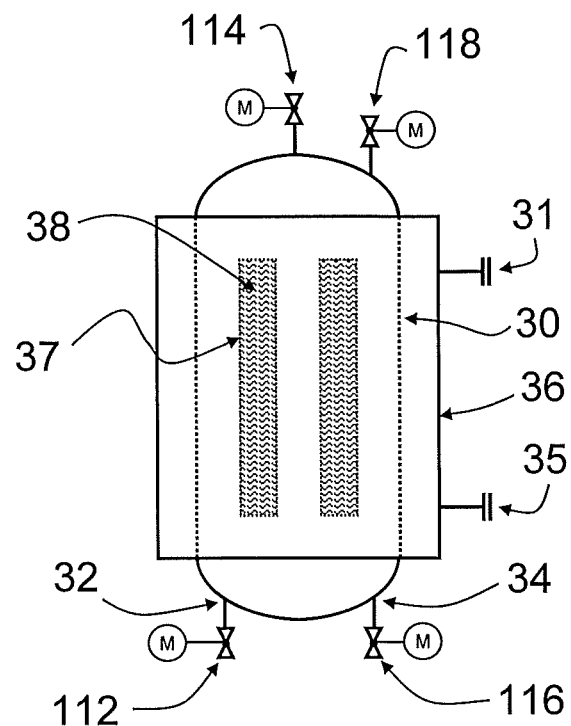
FIG. 3 is an illustration showing an "adsorber" that contains specialized media for removal of biogas contaminants which is regenerated by a hot inert gas stream.

As shown in FIG. 1, low moisture containing raw biogas 12 is delivered to a first stage compressor 15. The raw biogas produced by a landfill or waste water treatment plant digester has moisture that must be removed prior to delivery to the first stage compressor 15. In the first stage compressor, the raw biogas 12 is compressed to a maximum pressure of approximately 100 psig.

The compressor biogas, designated 18, is hot and delivered via a first conduit 19 to a first stage heat exchanger 20 where heat is removed and cooled. The cooled biogas, now designated 24, from the first stage heat exchanger 20 is then delivered to an exchanger/economizer 75 via a second conduit 21 where it is further chilled and condenses to remove the moisture. A chiller 72 is provided that recirculates cold fluid to and from the exchanger/economizer 75 via fourth and fifth conduits 76 and 77, respectively. After chilling in the exchanger/economizer 75, the cooled biogas 24 is then at ambient temperature and is re-heated and then delivered to the absorber 30 via a third conduit 22.

Cool outside atmospheric air 13 is used as a cooling fluid and delivered to the first stage heat exchanger 20. From the first stage heat exchanger 20, the heated air 27 is then delivered via the second conduit 23 to the exchanger/economizer 75. The heated air 27 is then delivered via a hot air conduit line 17 that is connected to a heat jacket 36 located on the adsorber 30.

The adsorber 30 includes a dry gas input port 32 which connects to the third conduit 22 connected to the exchanger/economizer 75. The biogas 24 travels upward in the adsorber 30 through an adsorption media 38 located inside at least one removable canister 37 located inside the adsorber 30. After traveling through the canister 37 and the adsorption media 38 contained therein, the biogas, is now "cleaned" biogas and designated by the reference number 29 exits the top of the adsorber 30 and travels via a sixth conduit 33 to a second stage compressor 50.

The adsorber 30 also includes an inert gas input port 34 which connects to an input inert gas conduit 39 that connects to an inert gas generator and VOC destruction unit 90. The inert gas generator and VOC destruction unit 90 produces a hot inert gas 42, such as carbon dioxide, which is capable of stripping contaminants from the adsorption media 38. The inert gas 42 is used to heat the adsorptive media 38 located in the canister 37. The inert gas 42 and the contaminants, designated 47, are then transferred from the adsorber 30 via a seventh conduit 43 back to the inlet port 99 on the inert gas generator and VOC destruction unit 90 where the contaminants are destroyed.

An important function of the inert gas generator and VOC destruction unit 90 is to purify the hot inert gas 42 so that it can be recycled through the conduits 39, 43, and 98 and thus re-used to regenerate the spent media in the adsorber 30. The inert gas generator 97 and VOC destruction unit 90 includes an air and gas mixture injection port 91, a burner 92, a media fill port 93, an outside air inlet 94, an outside vent or heat recovery port 95 and on outlet port 96. The hot inert gas 42 is produced by the inert gas generator and VOC destruction unit 90 and delivered to the adsorber 30 via conduit 98. A blower 48 may be used to forcibly deliver the hot inert gas 42 to the adsorber 30 through a heat exchanger 45 and conduit 39 at inlet port 34. Any excess amount of hot inert gas 42 produced by the inert gas generator/VOC destruction unit 90 may be discharged into the atmosphere through a discharge conduit 46. The hot inert gas 42 has relatively low concentration of oxygen thereby reducing the risk of unwanted combustion upstream of the inert gas generator and VOC destruction unit 90.

The adsorber 30 removes contaminants, including VOCs, siloxanes, organic sulfur compounds, and halogenated compounds from the dry and clean biogas 24. The adsorber 30 has an outer heat exchange jacket 36 which receives cool, outside air 13 or return heated air 27, 57, 67 from the three heat exchangers 20, 54, and 66, respectively. The heated air 27, 57, 67 from the three heat exchangers 20, 54, and 66, respectively, flows through the jacket 36 and is then either released into the atmosphere or is ported to another heat recovery device (not shown).

After the biogas has made its sojourn from the first stage of compression through the cooling, chilling, reheating and purification steps, the biogas 29 from the adsorber 30 is delivered to a second stage compressor 50 which compresses the biogas 29 from 100 psig to approximately 200 psig. From the second stage compressor 50, the compressed cleaned biogas, now designated 52, is then delivered to a second stage heat exchanger 54 where excess heat is again removed. The cooled cleaned biogas, now designated by the reference number 56, from the second stage heat exchanger 54 is then delivered to a third stage compressor 60 where it is pressurized to approximately 300 psig. A heat conduit 58 is used to deliver the heated fluid 57 from the second heat exchanger 54 to the heat exchanger jacket 36 through conduit 17. The compressed cleaned biogas 56 from the third stage compressor 60 is then delivered to the third stage heat exchanger 66 where excess heat is again removed. A heat conduit 64 is used to deliver the heated fluid 67 from the third heat exchanger 66 to the heat exchanger jacket 36 through conduit 17. The cooled biogas, now designated 70, is then released from the third stage heat exchanger 66 at pressure and delivered to a collection vessel, power generation device, or burned in a combustion device.

During operation of the system 10, the adsorber 30 must be taken out of service and hot inert gas 42 generated in the inert gas generator 90 must be delivered to the adsorber 30. Concurrently, the heat and air from the first heat exchanger 20, the first and second heat exchangers, 20 and 54 or the first, second and third heat exchangers 20, 54, 66, respectively, are sent through the external heat jacket 36 on the adsorber 30 to expedite the heating process.

In the embodiment shown, outside air 13 is routed through the external heat jacket 36 of adsorber 30 to help cool the adsorber 30.

The system includes a plurality of valves 112, 114, 116, 118 located in conduits 22, 33, 39, and 43, respectively, and that controls the flow of biogas or inert gas to the absorber 30, to the first heat exchanger 20, the first stage compressor 50, and the inert gas generator/VOC destruction unit 90, respectively. The valves 112, 114, 116 and 118 connect to and actuated by a control panel 80. During operation, the valves 112, 114, 116, and 118 are opened and closed by a control panel 80 so that during one phase of system operation the biogas flows continuously in the system 10 and the carbon media 38 inside the adsorber 30 is sufficiently cooled with outside air and return heated air.

In the embodiment shown in the accompanying FIG. 1, only one adsorber 20 is shown. It should be understood however, that the system 10 can be used with multiple absorbers. For example, a second adsorber (not shown) could be provided that processes the compressed biogas 18 from the first stage of compressor 15 until it reaches it's timed out period. The control panel 80 starts its regeneration. The valves 112, 114, 116, and 118, are automatically closed and opened, and the original adsorber 30 is placed on line.

Figure 4:
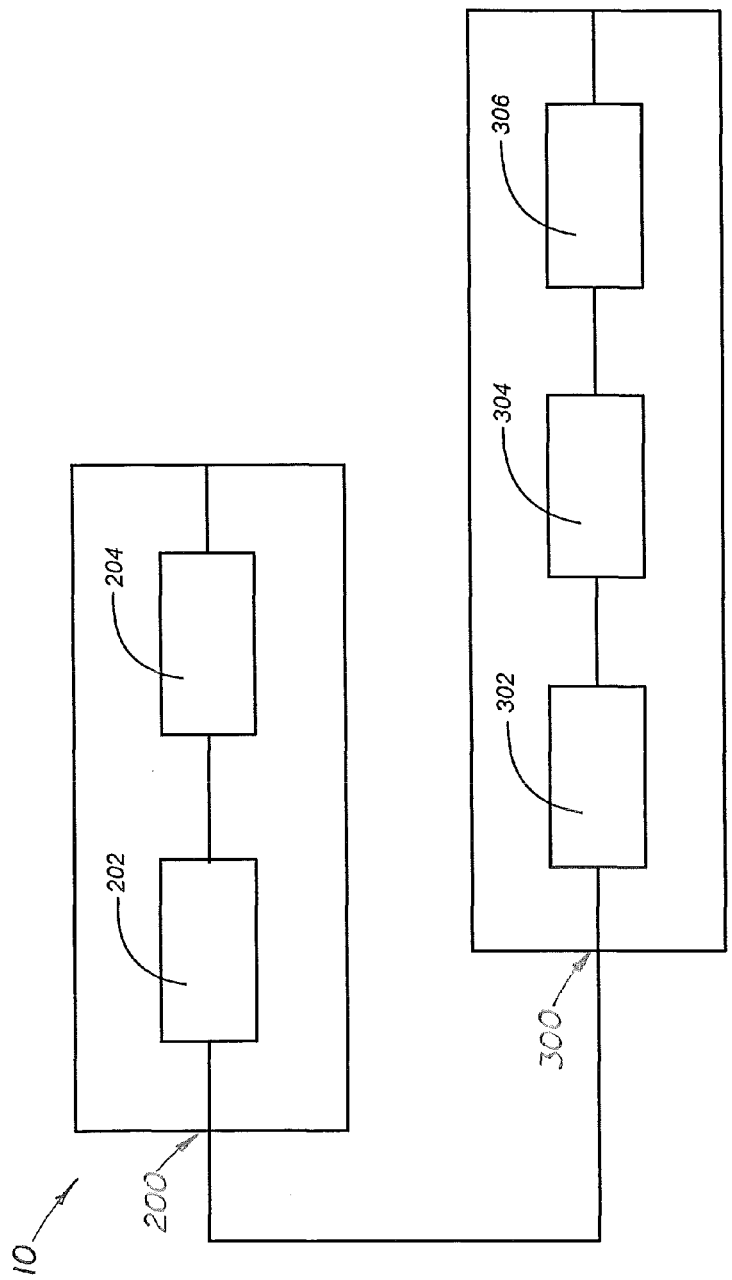
FIG. 4 is an illustration showing the biogas treatment system with a plurality of adsorbers aligned in a series.

As shown in FIG. 4, the system 10 could include several trains 200, 300 with two or three absorbers 202, 204, and 302, 304, 306, respectively, aligned in a series in each train. In such a system, when the gas contamination reaches a specific level, more than one adsorber is used in a train. If the biogas contaminants are at a high level, a train cannot last for more than, say 7 hours before its carbon media needs to be regenerated. In this instance, several trains would be necessary. The first train is allowed to process biogas until its carbon or other media is spent. The second absorber is then placed on line while the first absorber is regenerated. The third absorber is the next in line, and will be operating while the second is being regenerated, and first train is being cooled and in standby mode.

Preliminary calculations show that the use of this recovered compressor heat can reduce the amount of energy that would otherwise have to be spent by heating air or inert gases through electrical coils or by burning part of the purified gas stream to generate hot, inert gas, by between 15% and 40%, depending on how the system is configured. Further, the use of this excess heat would also reduce the heat-up time, thereby decreasing the time interval between purification campaigns. Further, because the cycle times between purification campaigns can be reduced, the size of the equipment can also be reduced, saving on both capital and O&M costs of the treatment equipment.

The above described system was originally conceived to utilize heat from the compression of low BTU fuel gases, such as landfill gas and municipal anaerobic digester to the pressure required by large gas-fired turbine generators for such fuels. Typically, this heat of compression is rejected to the atmosphere by the use of open heat exchangers, similar to the radiators in automobiles. In this case, typically the hot gas passes through finned tubes and is cooled by a large fan blowing air across them. Normally, one stage of compression will elevate the pressure of a gas from a fraction of a psig and around 100 degrees F. to approximately 125 psig and a temperature over 350 degrees F.

Compressing the gas beyond this pressure in a single stage produces diminishing returns from an efficiency and cost perspective. The gas must be cooled back to nominally 90 degrees F. before it can be compressed again in subsequent stages. Large power generation turbines require low BTU (nominal 50% methane) gas to be compressed to 250 psig or 350 psig with each stage of compression boosting the gas approximately 125 psig.

Due to on-board heat rejection equipment and losses through natural convection, the gas from each stage of compression is nominally around 200 degrees F. It is the heat in the gas at this temperature we wish to harvest and use in our gas purification process.

Of particular interest to the inventor are treatment systems for the removal of organosilicons in the form of siloxanes, silanes, silanols, halosilanes, and halosilanols. These contaminants are virtually ubiquitous in biogas, originating from various personal care products and industrial chemicals. These organosilicons impart silicon dioxide and silicates upon combustion of fuel gases containing them. The damage from the organosilicons can cause expensive damage to power generation equipment or even cause its total failure.

A recent development in the area of biogas treatment equipment is the use of systems that contain media and are regenerable by the use of either hot air or hot gases. The use of energy in these systems robs this energy from the power generation process. In addition, gas conditioning systems are most often required that also rob energy that could be sold for a profit. This invention enables the moisture removal equipment and gas treatment equipment processes to be modified so that they are smaller, operate more efficiently, and use less power.

Until now, the heat of compression of gases, and especially landfill gases, has been either wasted to the atmosphere or only partially utilized for re-heating gases after chilling to remove moisture. This invention captures the compressor heat and coveys it to specific parts of a biogas treatment system in order to improve its efficiency and cost of operation. In addition, this invention enables the cost of the gas or vapor treatment system itself to be reduced.

In summary, the above described system have the following benefits:

1) reduces the equipment size in comparison to other types of treatment;
2) lowers the capital cost compared to other technologies;
3) lowers the cost to operate compared other technologies; and
4) reduces the emissions to atmosphere compared to other technologies.

In compliance with the statute, the invention described herein has been described in language more or less specific as to structural features. It should be understood however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

We claim:

1. A system for utilizing the heat produced by compressing gas in a biogas treatment plant, comprising:
   a. a source of contaminated biogas;
   b. a first stage gas compressor connected to said biogas source used to compress biogas from said source of contaminated biogas;
   c. a first stage heat exchanger connected to an outside air source and to said first stage gas compressor, wherein the air from an outside air source is used to cool said compressed gas from said first stage gas compressor;
   d. a heat exchanger/economizer used to remove moisture from the biogas and reheat it to prevent condensation downstream in the treatment process; and which is supplied chilled fluid from a refrigerated chilling circuit and heated air from the first stage compressor;
   e. an adsorber connected to said first stage heat exchanger used to strip contaminants from said cooled compressed air from said first stage heat compressor, said adsorber including a media used to remove contaminates from said biogas, said absorber includes a conduit that carries an inert gas and contaminates away from said absorber;
   f. a second stage gas compressor connected to said adsorber to receive treated gas from said adsorber;
   g. a second stage heat exchanger connected to said second stage compressor to receive compressed treated gas therefrom, said second heat exchanger being connected to said adsorber to deliver heated air thereto;
   h. a third stage compressor connected to said second stage heat exchanger to receive cooled treated air from said second stage heat exchanger;
   i. a third stage heat exchanger connected to said third stage compressor, said third stage heat exchanger also being connected to an outside air source to deliver cool air thereto, said third stage heat exchanger also connected to said adsorber to deliver waste heat collected by said third stage exchanger to said adsorber; and,
   k. an inert gas generator and VOC destruction unit used to generate hot inert gas, said inert gas generator and VOC destruction unit includes a burner that produces hot inert gas used to remove contaminates collected by said adsorber from said biogas, said inert gas generator and VOC destruction unit also includes an heat exchanger that is coupled to said conduit that carriers insert gas and contaminants from said adsorber, said heat exchanger used to remove heat from said inert gas and said contaminants from said adsorber thereby reducing the amount of energy used by said system, said inert gas generator and VOC destruction unit also connected to said absorber so that inert gas containing contaminants purged from spent media in said adsorber is burned in said inert gas generator.

2. The system as recited in claim 1, wherein said first stage compressor compresses the biogas to a pressure of up to 100 psig, said second stage compressor compresses the treated biogas from the first stage compressor to a pressure up to 200 psig, and said third stage compressor compresses the treated biogas from the second stage compressor to a pressure up to 300 psig.

3. The system as recited in claim 1, wherein said adsorber includes at least one canister filled with media used to remove contaminants from said cool raw gas delivered to said adsorber.

4. The system as recited in claim 3, wherein said media is made of activated carbon particles or other suitable material.

5. The system as recited in claim 2, further including a valve disposed between said inert gas generator and said adsorber to control the flow of inert gas to said adsorber.

6. The system as recited in claim 1, further including a valve disposed between said first stage heat exchanger and said adsorber to control the flow of cooled biogas from said first stage heat exchanger and said adsorber.

7. The system, as recited in claim 1, further including a valve disposed between said second stage heat exchanger and said adsorber to control the flow of cooled biogas from said second stage heat exchanger and said adsorber.

8. The system as recited in claim 1, further including a valve disposed between said third stage heat exchanger and said adsorber to control the flow of cooled biogas from said third stage heat exchanger and said adsorber.

9. The system as recited in claim 1, further including a valve disposed between said inert gas generator and said adsorber to control the flow of inert gas to said adsorber.

10. A system for utilizing the heat produced by compressed gas in a biogas treatment plant, comprising:
   a. a contaminated biogas source;
   b. an adsorber connected to said biogas source, said adsorber containing a heat exchange jacket and media located in the adsorber for cleaning the biogas delivered to said adsorber;
   c. a plurality of gas compressors each capable of compressing the biogas delivered thereto;
   d. a plurality of heat exchangers each connected to one said gas compressor, said heat exchangers being used to extract heat from the biogas compressed by said gas compressor; and;
   e. an inert gas source connected to said absorber used to create a heated inert gas used to remove contaminants from said media, said inert gas source includes an heat exchanger that is connected to said absorber so that inert gas containing contaminants exiting said absorber may be returned to said inert gas source and combusted and used to generate heat to create said inert gas.

11. The system as recited in claim 10, further including a conduit system used to transfer the heat from one or more heat exchangers to said adsorber.

12. The system as recited in claim 10, wherein said media is made of carbon particles or other suitable media.

13. The system as recited in claim 10, wherein said inert gas produced by said inert gas source is carbon dioxide.

14. The system as recited in claim 11, wherein said media is made of carbon particles or other suitable media.

15. The system as recited in claim 11, wherein said inert gas produced by said inert gas source is carbon dioxide.

16. A method of recovering an adsorber filled with media used to remove contaminants in biogas treatment plant, comprising the following steps;
   a. selecting a system that includes an adsorber containing media used to remove contaminants from biogas, said absorber connected to a biogas delivery conduit with at least one compressor connected thereto used to pressurize said biogas, said system also includes a heat exchanger coupled to said compressor so that heat from said compressed biogas may be collected, said system also includes a heated inert gas generator capable of producing heated inert gas used to remove contaminants from said media inside said absorber when delivered thereto;
   b. delivering contaminated biogas to said compressor where said biogas is pressurized;
   c. delivering said compressed gas to said adsorber containing media that removes contaminates from said biogas;
   d. monitoring said media in said adsorber to determine if said media needs to be recycled;
   e. activating said heated inert gas generator to produce hot inert gas;
   f. delivering said hot inert gas from said inert gas generator to said adsorber to remove contaminants from said media;
   g. allowing said media to cool; and,
   h. repeating steps b thru g until all of the biogas has been processed.

17. The method as recited in claim 16, further including step of returning said inert gas used to heat said media in said absorber to said heated inert gas generator where it undergoes combustion.

18. A system for utilizing the heat produced by compressing gas in a biogas treatment plant, comprising:
   a. a source of contaminated biogas;
   b. a source of outside air;
   c. a first stage gas compressor connected to said source of contaminated biogas to compress the biogas from said source of contaminated biogas;
   d. a first stage heat exchanger connected to said first stage gas compressor and said source of outside air, wherein the air from said source of outside air is used to cool said compressed biogas from said first stage gas compressor;
   e. a heat exchanger/economizer connected said first stage heat exchanger to receive cooled biogas therefrom, said heat exchanger/economizer used to remove moisture and reheat said biogas thereby preventing excessive condensation;
   f. an adsorber connected to said heat exchanger/economizer to receive biogas therefrom, said absorber also connected to said first stage heat exchanger to received warm outside air therefrom, said adsorber including at least one canister containing absorption media used to remove contaminates from said biogas;
   g. an inert gas generator and VOC destruction unit connected to said adsorber, said inert gas generator and VOC destruction unit used to generate hot inert gas used to remove contaminants collected on said absorbent media in said adsorber, said inert gas generator and VOC destruction unit also includes an heat exchanger coupled to said adsorber to remove heat from said inert gas and said contaminants from said adsorber, said said inert gas generator and VOC destruction source unit also connected to said absorber so that inert gas containing contaminants purged from spent media is returned to said inert gas generator and VOC destruction device and burned;
   h. a second stage gas compressor connected to said adsorber to receive treated biogas from said adsorber;
   i. a second stage heat exchanger connected to said second stage compressor to receive compressed treated biogas therefrom, said second heat exchanger being connected to said adsorber to deliver cooled treated biogas thereto;
   j. a third stage compressor connected to said second stage heat exchanger to receive cooled treated air from said second stage heat exchanger; and,
   k. a third stage heat exchanger connected to said third stage compressor, said third stage heat exchanger also being connected to an outside air source to deliver cool air thereto, said third stage heat exchanger also connected to said adsorber to deliver waste heat collected by said third stage exchanger to said adsorber.

* * * * *